United States Patent [19]

Georgiev et al.

[11] Patent Number: 4,754,042

[45] Date of Patent: Jun. 28, 1988

[54] 5-{[NAPHTHYL(OR 2-OXO-1,3-BENZOXATHIOL-6-YL)OXY]METHYL}-3-PHENYL-3-(1H-IMIDAZOL-1-YLMETHYL)-2-METHYLISOXAZOLIDINES

[75] Inventors: Vassil S. Georgiev, Penfield; George B. Mullen, Avon, both of N.Y.

[73] Assignee: Pennwalt Corporation, Philadelphia, Pa.

[21] Appl. No.: 104,627

[22] Filed: Oct. 2, 1987

[51] Int. Cl.$^4$ .................... A61K 31/41; C07D 261/00
[52] U.S. Cl. .................... 548/240; 548/242; 549/32; 549/33
[58] Field of Search .............. 548/240, 242, 165; 514/378; 549/32, 33

[56] References Cited

U.S. PATENT DOCUMENTS

| | | | |
|---|---|---|---|
| 3,709,901 | 1/1973 | Draber | 548/235 |
| 3,711,495 | 1/1973 | Kulsa | 548/242 |
| 3,915,978 | 10/1975 | Kulsa | 548/240 |
| 3,987,179 | 10/1976 | Nadelson | 548/243 |
| 4,010,176 | 3/1977 | Kulsa | 548/242 |
| 4,510,154 | 4/1985 | Yoshida | 514/365 |

FOREIGN PATENT DOCUMENTS

| | | | |
|---|---|---|---|
| 171137 | 2/1986 | European Pat. Off. | 548/215 |
| 79-56726 | 6/1979 | Japan . | |

OTHER PUBLICATIONS

Sokolov, S. V. (1961), Chem. Abstract 55:7399.
Kano, H. (1965), Chem. Abstract 62:9139a.
Kano, H. (1965), Chem. Abstract 63:8367a.
Takahi, Y. (1974), Chem. Abstract 81:22233c.
Boyce, C. B. (1977), Chem. Abstract 87:23258a.
Funaki, Y. (1980), Chem. Abstract 92:128915u.
Kelly, R. C. (1980), Chem. Abstract 93:114498u.
Haken, P. T. (1980), Chem. Abstract 93:132471i.

*Primary Examiner*—Donald G. Daus
*Assistant Examiner*—Mark W. Noel

[57] ABSTRACT

5-{[Naphthyl(or 2-oxo-1,3-benzoxathiol-6-yl)oxy]methyl}-3-phenyl-3-(1H-imidazol-1-ylmethyl)-2-methylisoxazolidines are useful as antifungal agents.

5 Claims, No Drawings

5-{[NAPHTHYL(OR 2-OXO-1,3-BENZOXATHIOL-6-YL)OXY]METHYL}-3-PHENYL-3-(1H-IMIDAZOL-1-YLMETHYL)-2-METHYLISOXAZOLIDINES

BACKGROUND OF THE INVENTION

This invention pertains generally to substituted 2-methylisoxazolidines and more specifically to 5-{[naphthyl(or 2-oxo-1,3-benzoxathiol-6-yl)oxy]methyl}-3-phenyl-3-(1H-imidazol-1-ylmethyl)-2-methylisoxazolidines which are useful as antifungal agents.

BRIEF SUMMARY OF THE INVENTION

In accordance with this invention there are provided compounds of the formula:

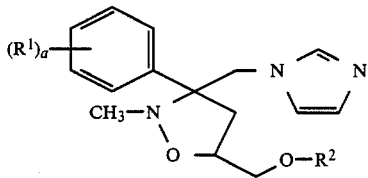

and the pharmaceutically acceptable acid addition salts thereof, in the form of their enantiomers or mixtures of their enantiomers including diastereomeric pairs of such enantiomers
wherein;
a = 1 or 2,
$R^1$ is selected from hydrogen, halogen, lower alkyl, lower alkoxy and combinations thereof, provided that the ortho position is hydrogen and
$R^2$ is selected from 1-naphthyl, 2-naphthyl, and 2-oxo-1,3-benzothiazol-6-yl.

DETAILED DESCRIPTION OF THE INVENTION

The compounds of this invention are useful as antifungal agents. They have been shown to exert in vitro activity against yeast and systemic mycoses and dermatophytes as determined by broth and agar testing techniques [McGinnis, M. R., *Laboratory Handbook of Medical Mycology*, Academic Press, New York, New York (1980)]. The compound prepared in Example 1 was found to have excellent to moderate inhibitory activity against a broad spectrum of fungi including *Trichophyton rubrum, Aspergillus fumigatus* and *Candida albicans* (minimum inhibitory concentration MIC, of <0.2 to 70 μg/ml).

Because of their antifungal activity, the compounds of the invention can be used, for example, in suitable liquid, semi-solid or solid carriers in the form of solutions, emulsions, suspensions, dispersions, ointments, aerosols, soaps, detergents, and powders in amounts effective to combat systemic dermatophylic fungal infections in warm blooded animals (1 to 20 percent active ingredient).

The compounds of this invention are those of the formula:

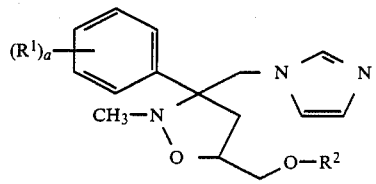

and the pharmaceutically acceptable acid addition salts thereof, in the form of their enantiomers or mixtures of their enantiomers including diastereomeric pairs of such enantiomers,
wherein;
a = 1 or 2,
$R^1$ is selected from hydrogen, halogen, lower alkyl, lower alkoxy and combinations thereof, provided that the ortho position is hydrogen, and
$R^2$ is selected from 1-naphthyl, 2-naphthyl, and 2-oxo-1,3-benzoxathiol-6-yl. By halogen is meant chlorine, bromine, fluorine and iodine, with chlorine and fluorine being preferred. By lower alkyl is meant alkyl groups having one to four (1-4) carbons and by lower alkoxy is meant alkoxy groups containing one to six (1-6) carbons. In either case such groups with three or more carbons can have a branched or unbranched chain.

The 5-{[naphthyl(or 2-oxo-1,3-benzoxathiol-6-yl)oxy]methyl}-3-phenyl-3-(1H-imidazol-1-yl-methyl)-2-methylisoxazolidine derivatives are obtained as mixtures of cis- and trans-diastereomers due to the presence of two asymmetric carbon atoms in the isoxazolidine ring. The diastereomeric mixture is conveniently separated by flash chromatography on silica gel using halogenated hydrocarbons (preferably dichloromethane and chloroform), alkanols (preferably methanol and ethanol), ethyl acetate and such, as eluents. The said eluents may be used alone or in combinations, such as the ones comprised of 95-99% halogenated hydrocarbon and 1-5% alkanol by volume. The stereochemistry of the two asymmetric carbon atoms in the isoxazolidine ring may be determined by conventional methods that include x-ray crystallography, nuclear magnetic resonance spectroscopy, circular dichroism and optical rotatory dispersion. Both the cis- and trans-diastereomers are resolvable into their optical enantiomers with (+)- and (−)-optical rotations by standard techniques such as fractional recrystallization of the diastereomeric salts with optically active organic acids such as (+)- and (−)-tartaric acid, (+)- and (−)-dibenzoyltartaric acid and the like.

As illustrated in the following diagram, the compounds of this invention can be prepared by an initial bromination of an appropriate acetophenone and reacting the resulting bromo derivative with imidazole to produce the 1-phenyl-2-(1H-imidazol-1-yl)ethanone. Reaction of the latter with N-methylhydroxylamine hydrochloride provides the 1-phenyl-2-(1H-imidazol-1-yl)-N-methylethanimine N-oxide (1) which is included in the subject matter of our co-pending application Ser. No. 900,856 filed August 1986 entitled "α-Substituted Ketonitrone Derivatives" whose disclosure is incorporated herein by reference.

The nitrone compound 1 is then treated with an appropriate 1-alkene derivative 2 to give a diastereomeric mixture of the desired cis- and trans-5-{[naphthyl(or 2-oxo-1,3-benzoxathiol-6-yl)oxy]methyl}-3-phenyl-3-(1H-imidazol-1-ylmethyl)-2-methylisoxazolidines 3.

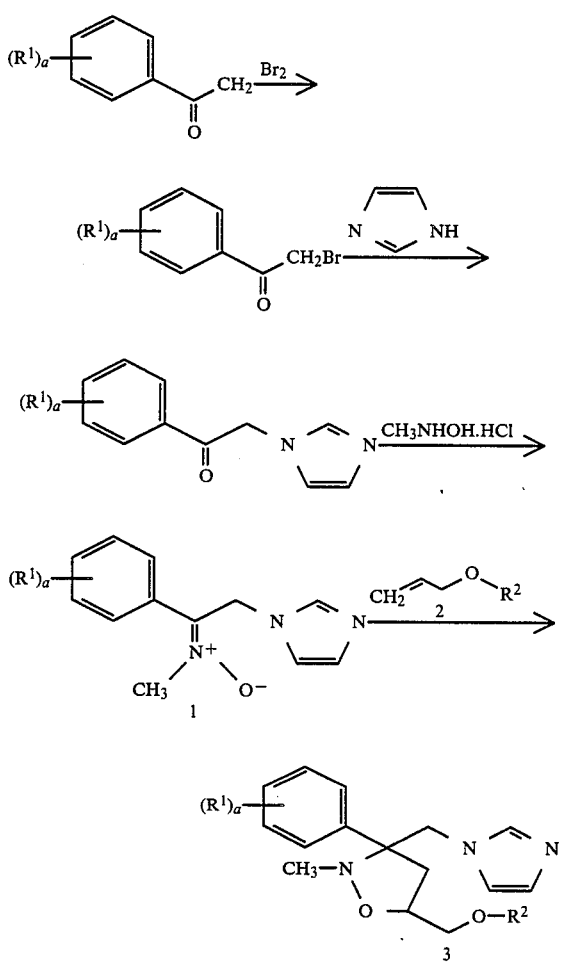

The compounds of this invention are basic and thus can form salts with pharmaceutically acceptable inorganic and organic acids such as, for example, acetic acid, maleic acid, malic acid, fumaric acid, succinic acid, succinamic acid, tartaric acid, citric acid, lactic acid, hydrochloric acid, hydrobromic acid, hydroiodic acid, nitric acid, sulfuric acid and phosphoric acid.

The preparation of the compounds of this invention is further illustrated by the following synthesis of intermediates and in the Examples.

PREPARATION OF ALLYL ARYL ETHERS 2

The allyl aryl ethers 2 can be prepared by the method of S. Mareinkiewicz, J., et al. *Tetrahedron*, 14, 208–22 (1961).

The following alkyl aryl ethers were synthesized:
6-(2-Propenoxy)-1,3-benzoxathiol-2-one (2: $R^2$=2-oxo-1,3-benzoxathiol-6-yl); yield: 61.5%; m.p. 78°–80° C. (ethyl ether).

2-(2-Propenoxy)naphthalene (2: $R^2$=2-naphthyl); yield: 76%; b.p. 75°–80° C. (0.05 mm).

1-(2-Propenoxy)naphthalene (2: $R^2$=1-naphthyl); yield: 74%; b.p. 75°–80° C. (0.05 mm).

EXAMPLE 1

3-(4-Fluorophenyl)-3-(1H-imidazol-1-ylmethyl)-2-methyl-5-{[(2-oxo-1,3-benzoxathiol-6-yl)oxy]methyl}isoxazolidine (3, $R^1$=4-F, $R^2$=2-oxo-1,3-benzoxathiol-6-yl)

A solution of 7.00 g (0.030 mol) of 1-(4-fluorophenyl)-2-(1H-imidazol-1-yl)-N-methylethanimine N-oxide (1, $R^1$=4-F) [prepared by reacting 2-(1H-imidazol-1-yl)-4'-fluoroacetophenone (17.24 g, 0.0844 mol), N-methylhydroxylamine hydrochloride (10.29 g, 0.123 mol) and sodium acetate (10.16 g, 0.124 mol) in 250 ml ethanol] and 6.56 g (0.0315 mol) of 6-(2-propenoxy)-1,3-benzoxathiol-2-one (2, $R^2$=2-oxo-1,3-benzoxathiol-6-yl) in 200 ml of toluene is heated to reflux under a nitrogen atmosphere and stirred for 48 hours, then cooled to ambient temperature and extracted with water (2×100 ml). The organic phase is dried over anhydrous magnesium sulfate and concentrated in vacuo to a dark oil containing a cis- and trans-diastereomeric mixture of compound 3 ($R^1$=4-F, $R^2$=2-oxo-1,3-benzoxathiol-6-yl), which is flash-chromatographed on neutral silica gel using ethyl acetate as the eluent.

Isomer A (4.75 g, 36%) has a melting point of 140°–142° C. (ethyl acetate). Anal. Calcd. for $C_{22}H_{20}FN_3O_4S$: C, 59.85; H, 4.57; F, 4.30; N, 9.52; S, 7.26. Found: C, 60.03; H, 4.59; F, 4.33; N, 9.48; S, 7.40.

EXAMPLE 2

3-(4-Fluorophenyl)-3-(1H-imidazol-1-ylmethyl)-2-methyl-5-{[(2-naphthyl)oxy]methyl}isoxazolidine (3, $R^1$=4-F, $R^2$=2-naphthyl)

Compound 3 ($R^1$=4-F, $R^2$=2-naphthyl) is prepared by a method similar to that described in Example 1 from 8.17 (0.035 mol) of 1-(4-fluorophenyl)-2-(1H-imidazol-1-yl)-N-ethanimine N-oxide (1, R=4-F) and 8.30 g (0.045 mol) of 2-(2-propenoxy)naphthalene (2, $R^2$=2-naphthyl) in 200 ml of toluene. The resulting cis- and trans-diastereomeric mixture of compound 3 ($R^1$=4-F, $R^2$=2-naphthyl) is flash-chromatographed on neutral silica gel using a 98:2 by volume mixture of chloroform and methanol as the eluent.

Isomer A (3.01 g, 20.6%) has a melting point of 160°–162° C. (ethyl acetate). Anal. Calcd. for $C_{25}H_{24}FN_3O_2$ (adjusted for 0.59% $H_2O$): C, 71.50; H, 5.82; F, 4.52; N, 10.01. Found: C, 71.33; H, 5.72; F, 4.50; N, 10.05.

EXAMPLE 3

3-(1H-Imidazol-1-ylmethyl)-2-methyl-5-{[(1-naphthyl)oxy]methyl}-3-phenyisoxazolidine (3, $R^1$=H, $R^2$=1-naphthyl)

Compound 3 ($R^1$=H, $R^2$=1-naphthyl) is prepared by a method similar to that described in Example 1 from 2-(1H-imidazol-1-yl)-N-methyl-1-phenylethanimine N-oxide (1, $R^1$=H) (10.28 g, 0.0477 mol) and 1-(2-propenoxy)naphthalene (2, $R^2$=1-naphthyl) (10.90 g, 0.0592 mol) in 200 ml of toluene. The resulting cis- and trans-diastereomeric mixture of compound 3 ($R^1$=H, $R^2$=1-naphthyl) is flash-chromatographed on neutral silica gel using a 98:2 mixture of chloroform and methanol as the eluent.

Isomer A (7.84 g, 41%) has a melting point of 42°–45° C. (ethyl acetate). Isomer A mononitrate salt has a melting point of 160°–163° C. (decomp.). Anal. Calcd. for $C_{25}H_{25}N_3O_2 \cdot HNO_3$: C, 64.92; H, 5.67; N, 12.11. Found: C, 64.85; H, 5.73; N, 12.15

EXAMPLE 4

3-(1H-Imidazol-1-ylmethyl)-2-methyl-5-[(naphthyloxy)methyl]-3-(substituted phenyl)isoxazolidines By following the method of Examples 2 and 3 and substituting for 1-(4-fluorophenyl)-2-(1H-imidazol-1-yl)-N-methylethanimine N-oxide one of the following compounds:

1-(4-methoxyphenyl)-2-(1H-imidazol-1-yl)-N-methylethanimine N-oxide, 1-(4-methylphenyl)-2-(1H-imidazol-1-yl)-N-methylethanimine N-oxide, 1-(4-chloro-3-methylphenyl)-2-(1H-imidazol-1-yl)-N-methylethanimine N-oxide, 1-(3,4-dichlorophenyl)-2-(1H-imidazol-1-yl)-N-methylethanimine oxide, 1-(3-methylphenyl)-2-(1H-imidazol-1-yl)-N-methylethanimine N-oxide, or 1-(3-methoxyphenyl)-2-(1H-imidazol-1-yl)-N-methylethanimine N-oxide, the corresponding 3-(1H-imidazol-1-ylmethyl)-2-methyl-5-[(naphthyloxy)methyl]-3-(substituted phenyl)isoxazolidines can be prepared.

Salts of the compounds of the invention can be prepared as known in the art, for example, by dissolving the compound in a 10:1 by volume mixture of ethanol and aqueous acid such as HCl or $HNO_3$, evaporating the solvent, and then recrystallizing the crude salt, for example, from methanol-ether, 1:3 by volume in the case of HCl salts, and ethanol in the case of $HNO_3$ salts.

We claim:

1. A compound of the formula:

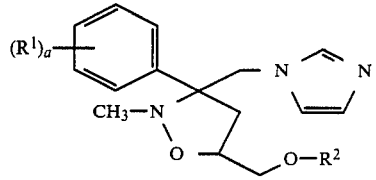

wherein, a = 1 or 2, $R^1$ is selected from hydrogen, halogen, lower alkyl, lower alkoxy and combinations thereof, provided that the ortho position is hydrogen, and $R^2$ is selected from 1-naphthyl, 2-naphthyl, and 2-oxo-1,3-benzoxathiol-6-yl.

2. The compound of claim 1 wherein the compound is 3-(4-fluorophenyl)-3-(1H-imidazol-1-ylmethyl)-2-methyl-5-{[(2-oxo-1,3-benzoxathiol-6-yl)oxy]methyl}isoxazolidine.

3. The compound of claim 1 wherein the compound is 3-(4-fluorophenyl)-3-(1H-imidazol-1-ylmethyl)-2-methyl-5-{[(2-naphthyl)oxy]methyl}isoxazolidine.

4. The compound of claim 1 wherein the compound is 3-(1H-imidazol-1-ylmethyl)-2-methyl-5-{[(1-naphthyl)oxy]methyl}-3-phenylisoxazolidine.

5. The compound of claim 1 wherein the compound is a 3-(1H-imidazol-1-ylmethyl)-2-methyl-5-[(naphthyloxy)methyl]-3-(substituted phenyl)isoxazolidine.

* * * * *